United States Patent
Bogdanov et al.

(10) Patent No.: US 6,284,220 B1
(45) Date of Patent: Sep. 4, 2001

(54) NONINVASIVE IMAGING OF NUCLEIC ACID VECTORS

(75) Inventors: Alexei Bogdanov, Arlington; Ching-Hsuan Tung, Natick; Ralph Weissleder, Charlestown, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/324,665

(22) Filed: Jun. 3, 1999

(51) Int. Cl.[7] ................................................ A61K 51/00
(52) U.S. Cl. ................ 424/1.73; 424/1.73; 424/1.11; 424/1.65; 424/1.69; 435/6; 435/7.1; 435/320.1; 435/5; 530/350; 530/224; 530/307; 534/10; 534/14; 534/15; 534/551; 514/455; 514/16; 514/17; 514/18; 514/12; 514/44; 536/23.1; 536/24.5; 549/280
(58) Field of Search ................... 424/1.65, 1.73, 424/1.69, 1.11; 549/280; 435/6, 7.1, 320.1, 5; 530/350, 224, 307; 514/455, 12, 44, 2, 16, 17, 18; 536/24.5, 23.1; 534/10, 14, 15, 551

(56) References Cited

U.S. PATENT DOCUMENTS

| 5,356,929 | 10/1994 | Heindel et al. | 514/455 |
| 5,473,083 | * 12/1995 | Heindel et al. | 549/280 |
| 5,714,328 | 2/1998 | Magda et al. | 435/6 |

FOREIGN PATENT DOCUMENTS

187332 * 7/1986 (WO).

OTHER PUBLICATIONS

Boris–Lawrie et al., "The Retroviral Vector", Ann. NY Acad. Sci., 716:59–71, 1994.
Curiel; "High–Efficiency Gene Transfer Mediated by Adenovirus–Polylysine–DNA Complexes", Ann. NY Acad. Sci. 716:36–58, 1994.
de Marco et al., "MR Imaging of Gene Delivery to the Central Nervous System With an Artificial Vector," Radiology, 208:65–71, Jul. 1998.
Dervan, Peter B., "Design of Sequence–Specific DNA–Binding Molecules", Science, 232:464–471, Apr. 25, 1986.
Felgner et al., "Cationic Liposome–Mediated DNA Transfection", Nature, 337:387–388, 1989.
Kayyem et al., "Receptor Targeted Co–Transport of DNA and Magnetic Resonance Contrast Agents," Chemistry & Biology, 2:615–620, 1995.
Mallinckrodt Technical Product Data sheet for Technescan® Gluceptate Kit (undated).
Palmer et al., "Instrumentation and Radiopharmaceuticals", in Practical Nuclear Medicine, W.B. Saunders Co., Philadephia, p. 27–69, 1992.
Schellingerhout et al., "Mapping the In Vivo Distribution of Herpes Simplex Virions", Human Gene Therapy, 9:1543–1549, Jul. 20, 1998.
Wiebe et al., "Radiopharmaceuticals to Monitor Gene Transfer", Nuclear Medicine, 41:79–89, 1997.
Wolff et al., "Injection of Naked Plasmid DNA", Science, 247:1465–68, 1990.

* cited by examiner

Primary Examiner—Karen Cochrane Carlson
Assistant Examiner—Hope A. Robinson
(74) Attorney, Agent, or Firm—Fish & Richardson P.C.

(57) ABSTRACT

Nucleic acid-imaging compositions and methods for noninvasive imaging of a nucleic acid introduced into somatic tissues of an animal or human are disclosed. The noninvasive imaging enables quantitative assessment of the biodistribution of the introduced nucleic acid. The disclosed imaging compounds include a base-binding moiety, a phosphate-binding moiety, and a metal-binding moiety. A chelated metal is non-invasively detected for imaging by radioactivity or magnetic resonance.

23 Claims, 5 Drawing Sheets

NONINVASIVE IMAGING OF NUCLEIC ACID VECTORS

FIELD OF THE INVENTION

The field of the invention is chemistry, molecular biology, gene therapy, radiology and medical imaging.

BACKGROUND OF THE INVENTION

Many diseases and disorders result from a genetic defect. In gene transfer therapy (often called simply "gene therapy"), an exogenous gene is introduced into somatic cells (as opposed to germ line cells) of an animal or human to substitute for, or compensate for, a defective gene.

Various methods for delivering exogenous genes into somatic cells of mammalian tissues have been developed. Examples of gene delivery methods include: injection of naked plasmid DNA (Wolff et al., 1990, *Science* 247:1465–68), cationic liposome-mediated DNA transfer (Felgner et al., 1989 *Nature* 337:387–388), retroviral vectors (Boris-Lawrie et al., 1994, *Ann. NY Acad. Sci.* 176:59–71), adenoviral vectors (Curiel, 1994, *Ann. NY Acad. Sci.* 176:36–58); microprojectiles, electroporation, and receptor-targeted co-transport of DNA and magnetic resonance contrast agents (Kayyem et al., 1995, *Chemistry & Biology* 2:615–620).

Regardless of the gene transfer method used, it is generally desirable for the researcher or clinician to be able to determine, noninvasively, where in the body the transferred gene went, and in what amount. Such information has been difficult to obtain. There is a need for methods of imaging the biodistribution of circular, double-stranded DNA by radioactivity or magnetic resonance.

SUMMARY OF THE INVENTION

DNA-imaging compositions and methods have been developed for noninvasive imaging of nucleic acid vectors, e.g., double-stranded, circular DNA vectors introduced into somatic tissues of an animal or human. The noninvasive imaging enables quantitative assessment of the biodistribution of the introduced nucleic acid.

The invention features a nucleic acid imaging compound that includes a base-binding moiety, a phosphate-binding moiety, and a metal-binding moiety. In some embodiments, the base-binding moiety intercalates between adjacent bases in double-stranded DNA. In some embodiments, the base-binding moiety forms a covalent bond with a base, e.g., upon irradiation with UV light.

Examples of base-binding moieties include psoralen, 8-methoxypsoralen, daunomycin, hycanthone, ethidium, methidium, acridine, acridine yellow, proflavin and propapyrroleindole. A preferred base-binding moiety is psoralen. Preferably, the phosphate-binding moiety bears a net positive charge, at physiological pH. Preferably, the phosphate-binding moiety contains one to six amino groups. Preferred types of phosphate-binding moieties are polyamines, polyimines and cationic polypeptides. Spermine is an example of a suitable polyamine. Pentalysine is an example of a suitable cationic polypeptide. Preferably, the metal-binding moiety forms a complex, e.g., a coordination complex or an ionic complex, with a metal or metal oxide. Examples of suitable metals and metal oxides are: $^{99m}Tc(V)O^{3+}$, $^{99m}Tc(IV)O^{2+}$, $111In^{3+}$, $Ga^{2+}$, Re, $Fe^{3+}$, $Gd^{3+}$, $D^{3+}$, $Mn^{2+}$, and lanthanides. Examples of metal binding moieties include: mercaptoacetyl-triglycyl; N-acetyl-glycyl-cysteinyl(S-acetamidomethyl)-glycyl-cysteinyl(S-acetamidomethyl)-glycyl; and glycyl-cysteinyl(S-acetamidomethyl)-glycyl; and glycyl-cysteinyl(S-acetamidomethyl)-glycyl-cysteinyl(S-acetamido-methyl)-glycyl.

In an exemplary embodiment of the invention, the base-binding moiety is psoralen, the phosphate-binding moiety is spermine, and the metal-binding moiety is mercaptoacetyl-triglycine. In another exemplary embodiment, the base binding moiety is psoralen, the phosphate-binding moiety is spermine, and the metal-binding moiety is N-acetyl-glycyl-cysteinyl(S-acetamidomethyl)-glycyl-cysteinyl(S-acetamidomethyl)-glycine. In another exemplary embodiment, the base intercalation moiety is psoralen, the phosphate-binding moiety is pentalysine, and the metal-binding moiety is glycyl-cysteinyl(S-acetamidomethyl)-glycyl-cysteinyl(S-acetamidomethyl)-glycine.

The invention also features a nucleic acid imaging composition, which includes a nucleic acid; and an imaging compound, as described above. In the nucleic acid imaging composition, the nucleic acid can be single-stranded or double-stranded, and it can be linear or circular.

The invention also features a method for non-invasive imaging of a nucleic acid. The method includes the following steps: providing a nucleic acid; providing an imaging compound (described above); combining the nucleic acid and the imaging compound to form a nucleic acid-imaging composition; combining the nucleic acid-imaging composition with a metal or metal oxide detectable by a noninvasive detector, thereby forming a labeled imaging composition; introducing the labeled imaging composition into a tissue; and imaging the nucleic acid with the noninvasive detector. The the nucleic acid can be single-stranded or a double-stranded, and it can be linear or circular. In some embodiments, the method includes the step of covalently binding the imaging compound to the nucleic acid, e.g., by irradiation with UV light. The detector may detect radioactivity or nuclear magnetic resonance, depending on whether the metal is paramagnetic or radioactive. The cell can be in an in vivo tissue, e.g., a somatic tissue in a mammal or human.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Although methods and materials similar or equivalent to those described herein can be used in the practice or testing of the present invention, the preferred methods and materials are described below. The materials, methods, and examples are illustrative only and not intended to be limiting. Other features and advantages of the invention will be apparent from the detailed description, and from the claims.

DETAILED DESCRIPTION

Figure 1:
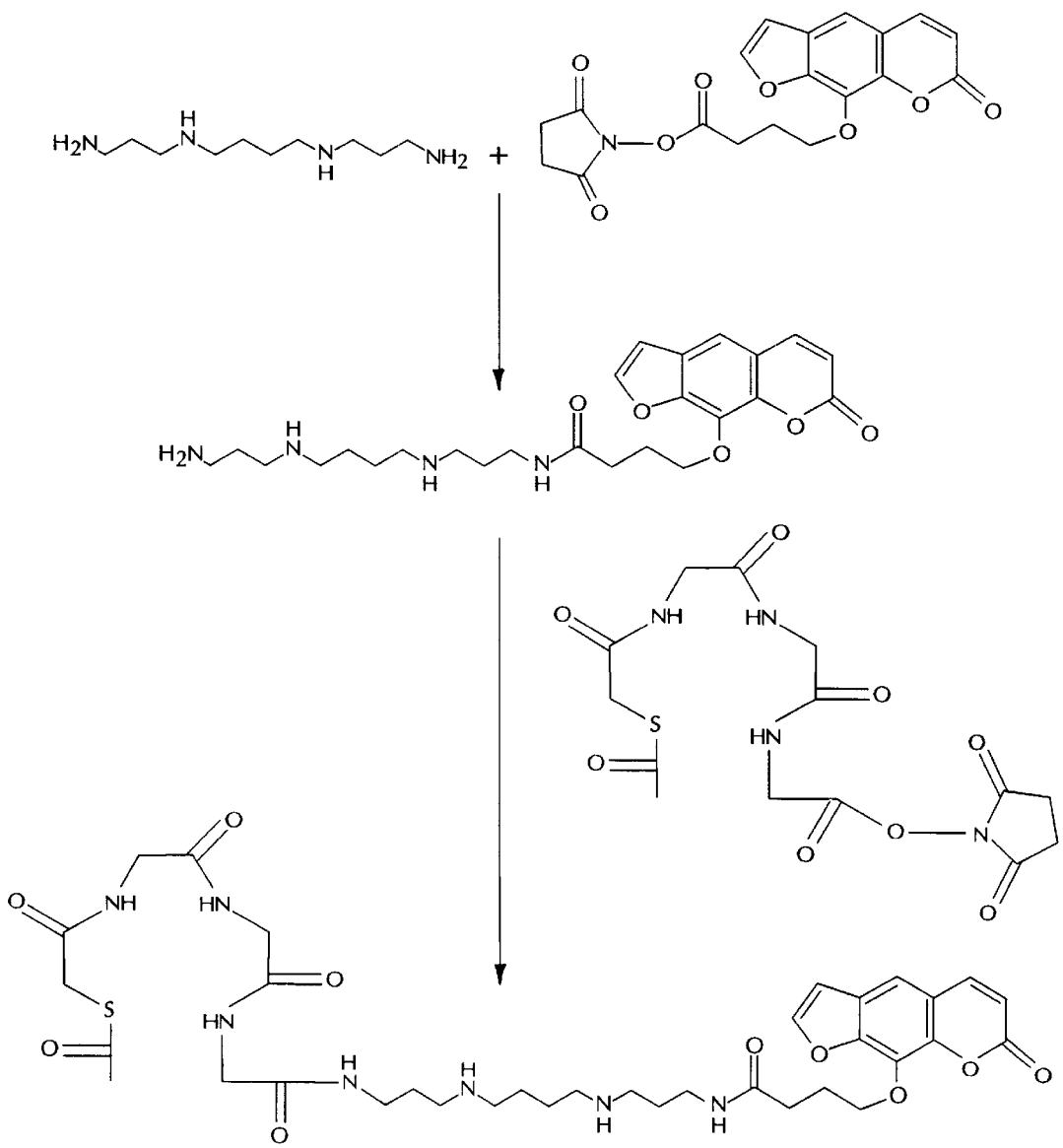
FIG. 1 is a diagram showing the scheme used for synthesis of mercaptoacetyl-triglycyl-spermine-butyrylpsoralene (Compound I).

A nucleic acid-imaging compound of the invention is contacted with, and bound to, a nucleic acid molecule, e.g., a gene therapy vector, to form a nucleic acid-imaging composition. The imaging composition is introduced into a tissue. The signal used for imaging is produced by a metal or metal oxide bound (chelated) by the imaging composition.

Each of the three moieties of the nucleic acid-imaging compound is designed for a particular function. The base-binding moiety has an affinity for the base portion of a nucleic acid. For example, it may insert (intercalate) between two successive bases in the double-helical structure of a double-stranded DNA molecule. The phosphate-binding moiety binds to phosphate portions of the nucleic acid, thereby contributing to the binding specificity and binding affinity of the imaging molecule for the nucleic acid. The metal-binding moiety binds or chelates the metal or metal oxide. The metal-binding moiety need not contribute to the specificity or affinity of the imaging molecule for the nucleic acid, although such a contribution is permissible. Below, each of the three moieties is discussed separately.

Various compounds suitable for incorporation as a base-binding moiety are known, many of which are commercially available. Examples of known compounds that intercalate into DNA, or otherwise bind to the base portion of a nucleic acid, include: psoralen, 8-methoxypsoralen, daunomycin, hycanthone, ethidium, methidium, acridine, acridine yellow, proflavin and propapyrroleindole. Novel base-binding compounds may be synthesized, or purified from natural sources. Such novel base-binding compounds can be incorporated into imaging compounds of the invention.

Psoralen, or a psoralen derivative, is a preferred base-binding moiety. For a discussion of psoralen intercalation into DNA, see, e.g., Anderson et al., 1980, *Ann. Rev. Pharm.* 20:235; and Berenbaum et al., 1981, *Science* 212:927.

Without intending to be bound by theory, the inventors note that intercalators for double-stranded DNA generally have planar, polycyclic, aromatic ring structures.

In some embodiments of the invention, the basebinding moiety remains usefully associated with a double-stranded DNA molecule without covalent bonding between the intercalation moiety and the DNA molecule. Such a useful association may be maintained, for example, by hydrogen bonding, van Der Waals interactions, or both. In some embodiments of the invention, after intercalation, a covalent bond forms between the intercalation moiety and a base in the DNA. Covalent bond formation can be triggered, for example, by ultraviolet light of a suitable wavelength and intensity. Psoralen is an example of an intercalation moiety that undergoes covalent bonding with DNA, when exposed to ultraviolet light. Some base-binding moieties display useful binding to bases in single-stranded nucleic acids.

Any of various phosphate-binding moieties can be incorporated in the present invention. Preferably, the phosphate-binding moiety does not form a covalent bond with the DNA. In preferred embodiments, the phosphate-binding moiety includes cationic groups that participate in electrostatic interactions with the anionic phosphate groups of the nucleic acid. Spacing between cationic groups on the phosphate-binding moiety can be designed to optimize eletrostatic interactions with the anionic phosphate groups. Exemplary types of phosphate-binding moieties are polyamines, polyimines and cationic polypeptides. An exemplary cationic polypeptide is an oligolysine. Specific examples of compounds that can be incorporated as phosphate-binding moieties include spermine and pentalysine.

Various metal-binding molecules or moieties are known, and can be incorporated into an imaging compound according to the invention, without undue experimentation. In addition, novel metal-binding moieties may be discovered and can be used in the invention. Preferably, the metal-binding moiety does not form a covalent bond with the metal. In preferred embodiments, the metal-binding moiety forms a thermodynamically and kinetically stable non-covalent coordination complex or ionic complex with $^{99m}$Tc(V)O$^{3+}$, $^{99m}$Tc(IV)O$^{2+}$, 111In$^{3+}$, Ga$^{2+}$, Re, Fe$^{3+}$, Gd$^{3+}$, Dy$^{3+}$, Mn$^{2+}$, other useful metal or metal oxide, or lanthanide.

Figure 2:
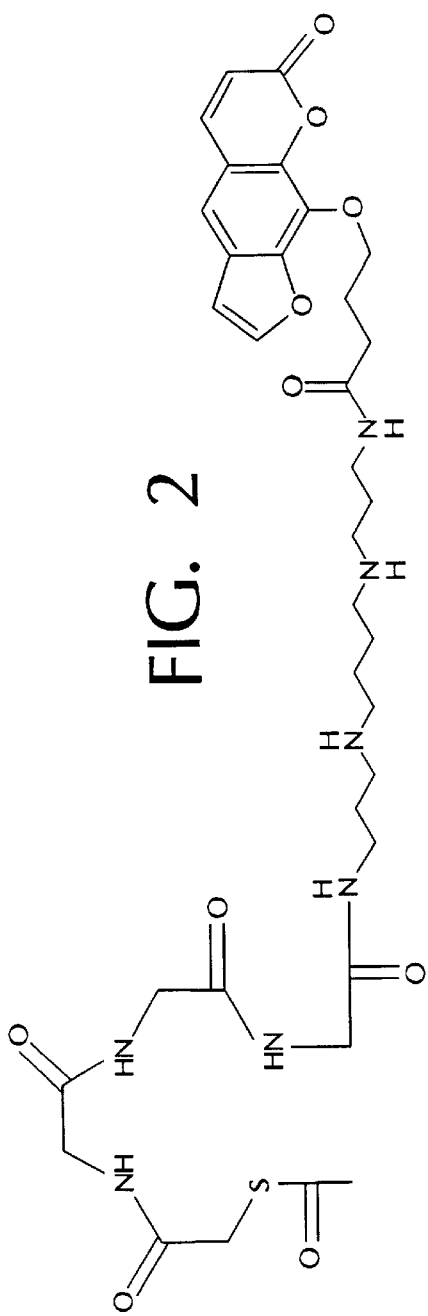
FIG. 2 is the chemical structure of mercaptoacetyl-triglycyl-spermine-butyrylpsoralene, which is an example of a nucleic acid imaging compound of the invention.
Figure 3:
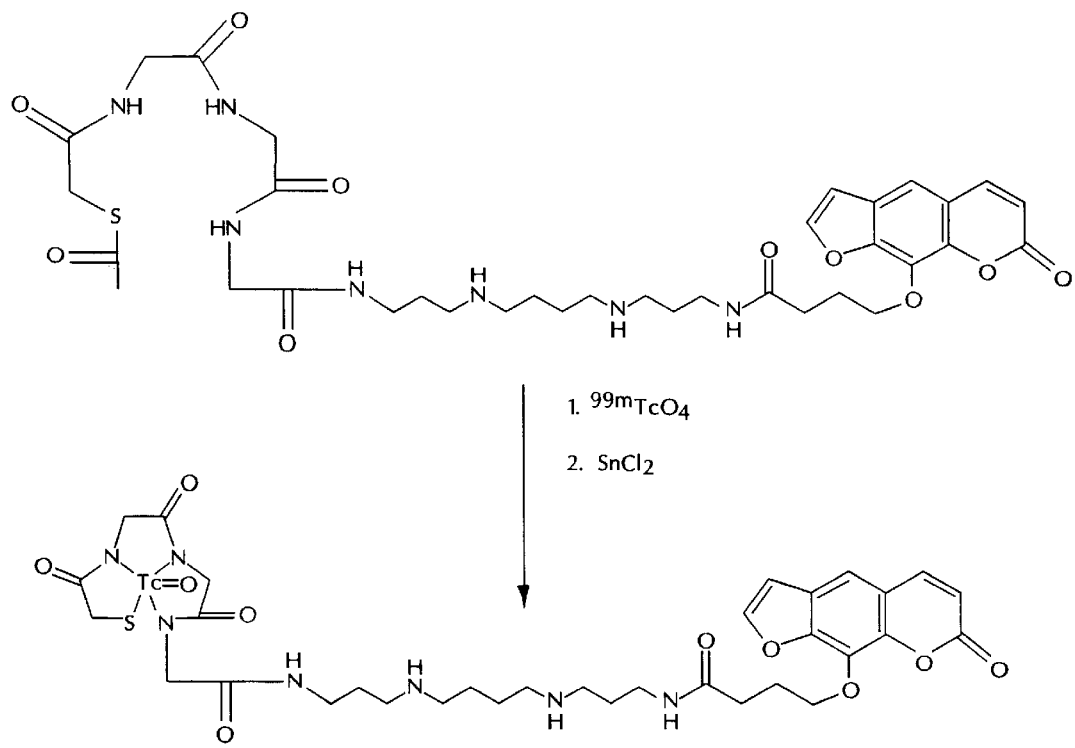
FIG. 3 is a diagram illustrating the radioactive labeling of Compound I with $^{99m}Tc$.

Examples of metal-binding moieties useful in the invention include a mercaptoacetyl-triglycyl moiety (FIG. 1); an N-acetyl-glycyl-cysteinyl(S-acetamidomethyl)-glycyl-cysteinyl(S-acetamidomethyl)-glycyl moiety (FIG. 2); and a glycyl-cysteinyl(S-acetamidomethyl)-glycyl-cysteinyl(S-acetamidomethyl)-glycyl moiety (FIG. 3). Examples of other useful metal-binding moieties include:

diethylenetriamine-pentaacetic acid (DTPA);
ethylenedicysteine;
1-imine-3-mercaptotutace;
bis(aminoethanethiol)carboxylic acid;
triethylenetetraamine-hexaacetic acid;
ethylenediamine-tetraacetic acid (EDTA);
1,2-diaminocyclohexane-N,N,N',N'-tetraacetic acid;
N,N'-di(2-hydroxybenzyl)ethylenediamine;
N-(hydroxy-ethyl)ethylenediaminetriacetic acid;
nitrilotriacetic acid;
ethylene-bis(oxyethylene-nitrilo)tetraacetic acid;
1,4,7,10-tetraazacyclodo-decane-N,N',N',N'''-tetraacetic acid;
1,4,7,10-tetraaza-cyclododecane-N,N',N''-triacetic acid;
1,4,7,-tris(carboxymethyl)-10-(2'-hydroxypropyl)-1,4,7,10-tetraazocyclodecane,
1,4,7,-triazacyclonane-N,N',N''-triacetic acid; and
1,4,8,11-tetraazacyclotetra-decane-N,N',N'',N'''-tetraacetic acid.

In the practice of this invention, in general, base-binding moieties are interchangeable, phosphate-binding moieties are interchangeable, and metal-binding moieties are interchangeable. Thus, numerous, different combinations of an base-binding moiety, a phosphate-binding moiety, and a metal-binding moiety are within the scope of the invention.

Each of the three moieties can be obtained commercially or synthesized according to conventional, organic chemical synthesis methods. Suitable covalent linkage of the three moieties can be carried out by one of skill in the art, employing conventional methods, without undue experimentation.

In some embodiments, the nucleic acid to which the imaging molecule is bound (to form an imaging composition) is double-stranded DNA. The DNA can be circular, e.g., a plasmid vector. Operation of the imaging compounds of the invention is not sequence-dependent. The imaging compounds can be used with a nucleic acid having essentially any length and nucleotide sequence. The design and construction of nucleic acid molecules, e.g., gene therapy vectors, is within ordinary skill in the art. For example, the construction of a model plasmid for gene delivery is described by de Marco et al., 1998, *Radiology* 208:65–71. For recombinant DNA methodology and vector construction, see generally, Sambrook et al., 1989, *Molecular Cloning: A Laboratory Manual*, Second Edition, Cold Spring Harbor, New York.

The invention is further illustrated by the following examples. The examples are provided for illustration purposes only, and are not to be construed as limiting the scope or content of the invention in any way.

EXAMPLE 1

N-(4-(psoralen-8-yloxy))-spermine-N'-mercaptoacetyl-triglycine

Succinimidyl-[4-(psoralen-8-yloxy)]butyrate was reacted with an equimolar amount of spermine tetrahydrochloride in water:DMF solution in the presence of triethylamine. Without purification, the resultant product was reacted with succinimidyl-acetomercaptoacetyl triglycine at equimolar ratio, to form N-(4-(psoralen-8-yloxy))-spermine-N'-mercaptoacetyl-triglycine ("Compound I"; FIGS. 1 and 2).

The reaction mixture was purified on a C-18 HPLC column, using a 0–80% acetonitrile gradient in 1% TFA. Fractions eluting as a separate peak at 45–50% acetonitrile were analyzed using thin layer chromatography (TLC), and then pooled.

Figure 4:
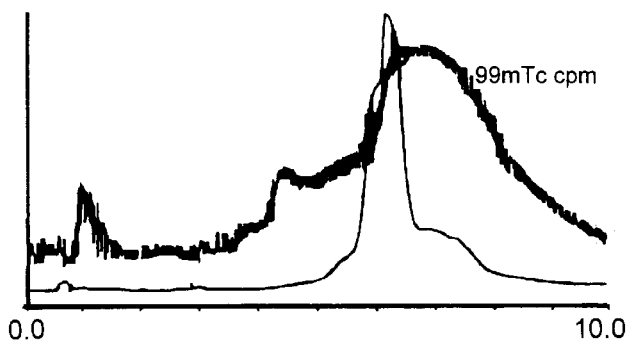
FIG. 4 is a chromatogram showing the results of HPLC analysis of the labeled Compound I.

Labeling was performed using [$^{99m}$Tc]O-tartrate complex. The labeling was accomplished by reduction of pertechnetate with Sn(II) in the presence of tartrate and ammonium acetate (for SH-group de-protection) at pH 8.5. Labeling resulted in 98.5% reduction of $^{99m}$Tc-pertechnetate, (by ITLC-G in acetone). HPLC revealed approximately 90% of the radioactivity to be associated with UV-positive fraction (FIGS. 3 and 4).

Incubation of the $^{99m}$Tc-labeled Compound I with plasmid DNA (pUHC-13-3, 5.16 kb and pCMV-GFP, 5.6 kb) at different stochiometric ratios. Stoichiometric ratios in the range of one molecule Compound I per 15 base pairs (in the DNA) to one molecule Compound I per 60 base pairs, showed some DNA condensation. This indicated neutralization of negative charge by the positively charged imaging-compound. The extent of condensation did not prevent complex formation with positively charged lipid and polymer carriers.

Irradiation of the labeled Compound I/DNA complex with UV light at 350 nm for 10 minutes resulted in binding of radioactivity to DNA (25% of total $^{99m}$Tc-added). Agarose gel electrophoresis revealed a single $^{99m}$TC-labeled plasmid DNA band. Electrophoresis of non-irradiated controls indicated little or no covalent binding between the intercalator and the DNA, i.e., less than 3% of the radioactivity remained associated with the DNA.

Comparative studies in rats showed good correlation between biodistributions of AT$^{32}$P-nick-translated plasmid and the plasmid labeled with Compound I at stochiometric ratios of 1:15 base pairs and 1:30 base pairs.

EXAMPLE 2

Figure 5:
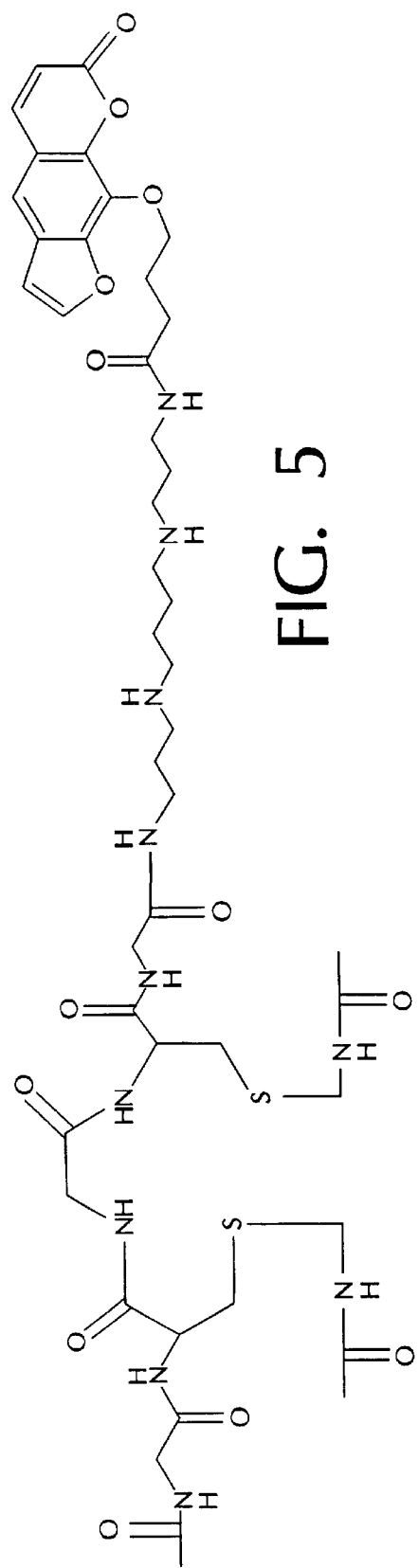
FIG. 5 is the chemical structure of N-acetyl-glycyl-cysteinyl(S-acetamidomethyl)-glycyl-cysteinyl(S-acetamidomethyl)-glycyl-spermine-butyrylpsoralene, which is an example of a nucleic acid-imaging compound of the invention.

N-acetyl-glycyl-cysteinyl(S-acetamidomethyl)-glycyl-cysteinyl(S-acetamidomethyl)-glycyl-spermine-butyrylpsoralene Succinimidyl-[4-(psoralen-8-yloxy)]butyrate was reacted with an equimolar amount of spermine tetrahydrochloride in water:DMF solution in the presence of triethylamine. The resultant product was used without purification and reacted with N-succinimidyl ester of N-acetylGly-Cys(Acm)-Gly-Cys(Acm)-Gly at equimolar ratio, to obtain N-acetyl-glycyl-cysteinyl(S-acetamidomethyl)-glycyl-cysteinyl(S-acetamidomethyl)-glycyl-spermine-butyrylpsoralene (FIG. 5). Reaction mixture was applied on C-18 HPLC column and eluted with 0–80% acetonitrile gradient in 1% TFA. Fractions eluted as a separate peak at 45–50% acetonitrile were analyzed using Silicagel thin layer chromatography (TLC), and pooled.

EXAMPLE 3

Psoralen-peptide Synthesis

Figure 6:
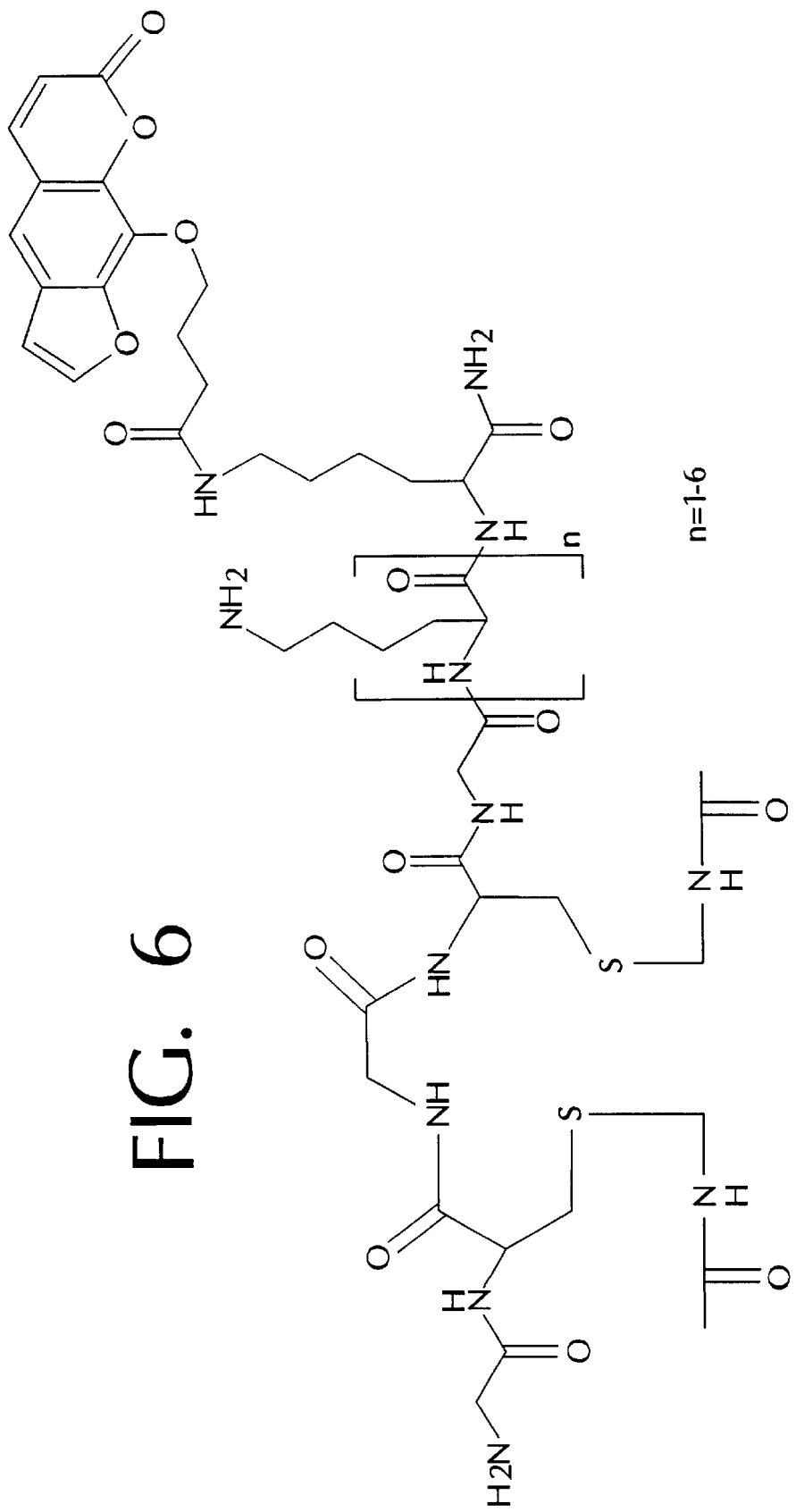
FIG. 6 is the chemical structure of glycyl-cysteinyl(S-acetamidomethyl)-glycyl-cysteinyl(S-acetamido-methyl)-glycyl-pentalysyl-butylpsoralene.

The pepetide was synthesized on an automatic synthesizer (PS3, Rainin, Woburn, Mass.) by Fmoc chemistry using 2-(1H-benzotriazole-1-yl)-1,1,3,3-tetramethyluronium hexafluorophosphate (HBTU)/N-hydroxybenzotriazole (HOBt) as activating agent. The sequence is Gly-Cys(Acm)-Gly-Cys(Acm)-Gly-Lys-Lys-Lys-Lys-Lys(Psoralen-NH$_2$ Fmoc-Lys (Dde) was anchored to 0.1 mmole of Rink amide MBHA resin (NovaBiochem, San Diego, Calif.) first and followed with other amino acids, e.g. Fmoc-Lys(Boc), Fmoc-Gly, Fomc-Cys(Acm) (All amino acids were purchased from Novabiochem (San Diego, Calif.). The N-terminal was finally capped with t-Boc-Gly. Thereafter the Dde group on the C-terminal lysine residue was selectively removed with 10 ml of 2% hydrazine in DMF (2×3 min) and the deprotected amino group was reacted with 0.4 mmole succinimidyl-[4-(psoralen-8-yloxy)]butyrate (Molecular Bioscience, Boulder, Colo.) in 5 mL of DMSO/diisopropylethylamine (20% v/v) overnight. The peptide (FIG. 6) was cleaved by 5 ml of TFA/thioanisole/ethandithiol/anisole (90/5/3/2), and purified by C18 reverse phase HPLC. MALDI-MS (M+H)$^+$: 1448.71 (calc.), 1449.23 (found).

EXAMPLE 4

Biodistribution of DNA vectors and DNA transfection complexes

Figures 7A, 7B:
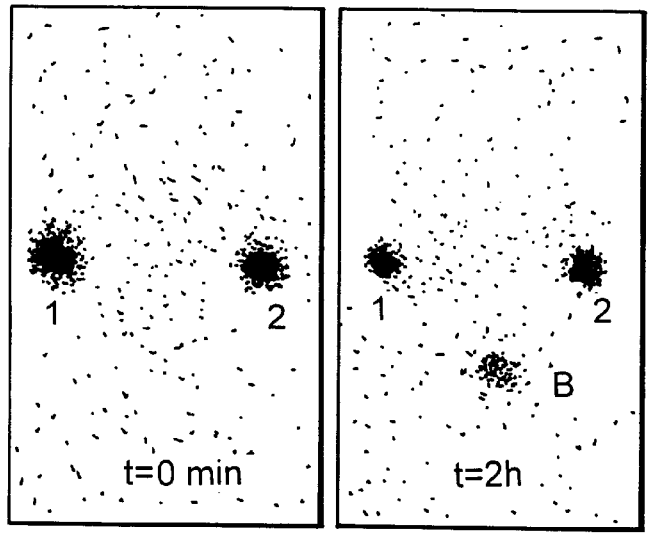
FIG. 7A is an image of 9L rat gliosarcoma flank tumors in a mouse immediately following injection of the tumors with double-stranded DNA labeled with $^{99m}$Tc. Tumor 1 was injected with labeled DNA only. Tumor 2 was injected with labeled DNA complexed with TransIT-100.
FIG. 7B is an image of the same tumors shown in FIG. 4A, two hours after injection of the labeled DNA.
Figure 8:
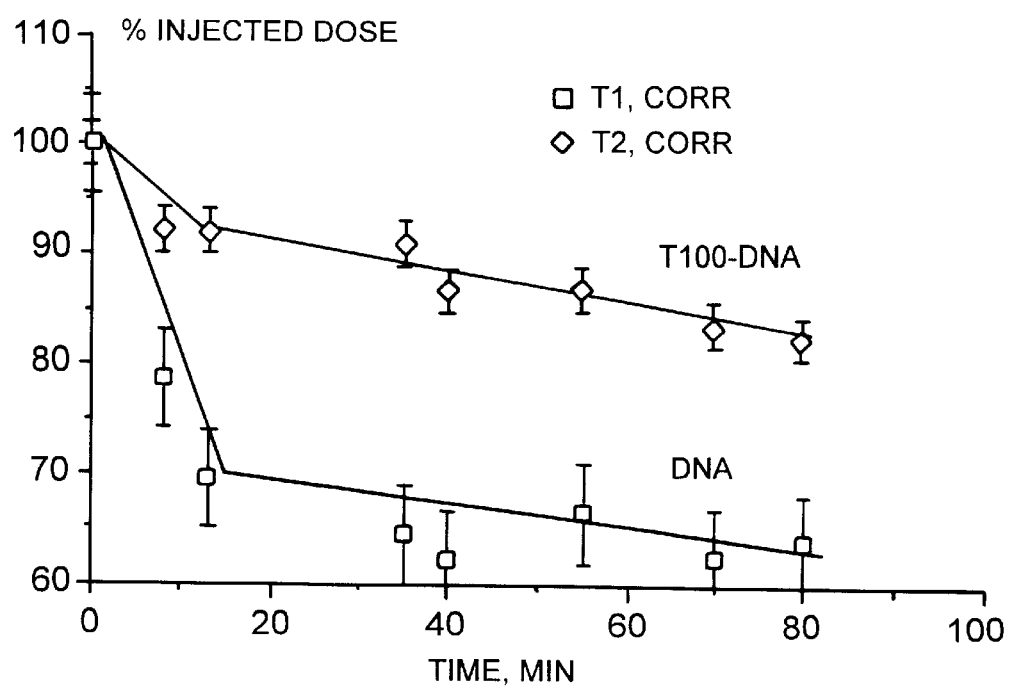
FIG. 8 is a graph illustrating the time course of DNA elimination from the site where a DNA imaging composition was injected into a mouse.

A complex between plasmid vector (pCMV-GFP) was obtained at a ratio of molecule Compound I per 30 base pairs of DNA (total 10 μg DNA) with the specific activity of 5 μCi $^{99m}$Tc/μg DNA. Labeled DNA was separated into two 5 μg aliquots and transfection reagent (cationic polymer TransIT-100, PanVera, Madison Wis.) was added 9L rat gliosarcoma tumors (diameter=0.5 cm) were grown in flanks of mice (nu/nu). Flank tumors were injected with identical volume and radioactivity of DNA. Tumor 1 was injected with labeled DNA only, and tumor 2 was injected with the complex of DNA and TransIT-100. The animal was anesthetized and imaged immediately and then for 2 hours, with 15 minute intervals (FIGS. 7A and 7B). Local changes in radioactivity within the tumor was monitored using region-of-interest approach. We observed a faster elimination of DNA from the tumor when the vector was injected by itself as compared to complexed with lipids (FIG. 8). The more rapid clearing was accompanied by gradual accumulation of the tracer in the bladder suggesting DNA degradation.

Other embodiments are within the following claims.

We claim:

1. A nucleic acid-imaging compound comprising: a base binding moiety comprising a planar, polycyclic aromatic ring structure that intercalates between bases in double-stranded DNA, a phosphate binding moiety selected from the group consisting of polyamines, polyimines and a cationic polypeptide, a metal binding moiety selected from the group consisting of a mercaptoacetyl-triglycyl moiety;

an N-acetyl-glycyl-cysteinyl(S-acetamidomethyl)-glycyl-cysteinyl(S-acetamidomethyl)-glycyl moiety;

a glycyl-cysteinyl(S-acetamidomethyl)-glycyl-cysteinyl(S-acetamidomethyl)-glycyl moiety;

a diethylenetriamine-pentaacetic acid (DTPA) moiety;

an ethylenedicysteine moiety;

a 1-imine-3-mercaptotutace moiety;

a bis(aminoethanethiol)carboxylic acid moiety;

a triethylenetetraamine-hexaacetic acid moiety;

a ethylenediamine-tetraacetic acid (EDTA) moiety;

a 1,2-diaminocyclohexane-N,N,N',N'-tetraacetic acid moiety;

a N,N'-di(2-hydroxybenzyl)ethylenediamine moiety;

a N-(hydroxy-ethyl)ethylenediaminetriacetic acid moiety;

a nitrilotriacetic acid moiety;

a ethylene-bis(oxyethylene-nitrilo)tetraacetic acid moiety;

a 1,4,7,10-tetraazacyclodo-decane-N,N',N",N'''-tetraacetic acid moiety;

a 1,4,7,10-tetraaza-cyclododecane-N,N',N"-triacetic acid moiety;

a 1,4,7-tris(carboxymethvl)-10-(2'-hydroxypropyl)-1,4,7,10-tetraazocyclodecane moiety;

a 1,4,7-triazacyclonane-N,N',N"-triacetic acid moiety; and a 1,4,8,11-tetraazacyclotetra-decane-N,N',N",N'''-tetraacetic acid moiety; and a radioactive or paramagnetic metal or metal oxide bound by the metal-binding moiety.

2. The compound of claim 1, wherein the base-binding moiety forms a covalent bond with a base, upon irradiation.

3. The compound of claim 2, wherein the base binding moiety is selected from the group consisting of: psoralen, 8-methoxypsoralen, daunomycin, hycanthone, ethidium, methidium, acridine, acridine yellow, proflavin and propa-pyrroleindole.

4. The compound of claim 3, wherein the base-binding moiety is psoralen.

5. The compound of claim 1, wherein the phosphate-binding moiety bears a net positive charge, at physiological pH.

6. The compound of claim 5, wherein the phosphate-binding moiety contains one to six amino groups.

7. The compound of claim 1, wherein the polyamine is spermine.

8. The compound of claim 1, wherein the cationic polypeptide is oligolysine.

9. The compound of claim 1, wherein the metal or metal oxide is selected from the group consisting of: 99mTc(V)O3+, 99mTc(IV)O2+, 111In3+, Ga2+, Re, Fe3+, Gd3+, Dy3+, Mn2+, and a lanthanide.

10. The compound of claim 1, wherein the metal-binding moiety comprises a structure selected from the group consisting of:

a mercaptoacetyl-triglycyl group;

an N-acetyl-glycyl-cysteinyl(S-acetamidomethyl)-glycyl-cysteinyl(S-acetamidomethyl)-glycyl group; and a glycyl-cysteinyl(S-acetamidomethyl)-glycyl-cysteinyl(S-acetamidomethyl)-glycyl group.

11. The compound of claim 1, wherein the base binding moiety is psoralen, the phosphate-binding moiety is spermine, and the metal-binding moiety is mercaptoacetyl-triglycine.

12. The compound of claim 1, wherein the base binding moiety is psoralen, the phosphate-binding moiety is spermine, and the metal-binding moiety is N-acetyl-glycyl-cysteinyl(S-acetamidomethyl)-glycyl-cysteinyl(S-acetamidomethyl)-glycine.

13. The compound of claim 1, wherein the base binding moiety is psoralen, the phosphate-binding moiety is pentalysine, and the metal-binding moiety is glycyl-cysteinyl(S-acetamidomethyl)-glycyl-cysteinyl(S-acetamidomethyl)-glycine.

14. A nucleic acid-imaging composition comprising a nucleic acid and an imaging compound of claim 1.

15. The composition of claim 14, further comprising a covalent bond between a base in the nucleic acid and the base-binding moiety of the imaging compound.

16. The composition of claim 14, wherein the nucleic acid is a circular, double-stranded DNA.

17. A method for imaging a nucleic acid, comprising:

providing a nucleic acid;

providing an imaging compound of claim 1;

contacting the nucleic acid with the imaging compound to form a nucleic acid-imaging composition;

contacting the nucleic acid-imaging composition with a metal or metal oxide detectable by a noninvasive detector, thereby forming a labeled imaging composition;

introducing the labeled imaging composition into a tissue;

imaging the nucleic acid with the noninvasive detector.

18. The method of claim 17, further comprising the step of covalently binding the imaging compound to the nucleic acid.

19. The method of claim 18, wherein the covalent binding step comprises irradiating the imaging compound with ultraviolet light.

20. The method of claim 17, wherein the nucleic acid is a circular, double-stranded DNA.

21. The method of claim 17, wherein the detector detects radioactivity or magnetic resonance.

22. The method of claim 17, wherein the cell is in an in vivo tissue.

23. The method of claim 22, wherein the tissue is in a mammal.

* * * * *